United States Patent

Palm-Plessmann et al.

[11] Patent Number: 5,940,470
[45] Date of Patent: Aug. 17, 1999

[54] MEDICAL X-RAY SYSTEM HAVING A COMMON SUPPORT AND A FURTHER COMPONENT FOR MOUNTING A RADIATION RECEIVER

[75] Inventors: Ulrike Palm-Plessmann, Fuerth; Claudius Molz, Buckenhof, both of Germany

[73] Assignee: Siemens Aktiengesellschaft, Munich, Germany

[21] Appl. No.: 08/939,445

[22] Filed: Sep. 29, 1997

[30] Foreign Application Priority Data

Sep. 27, 1996 [DE] Germany ............................ 196 39 977

[51] Int. Cl.⁶ ...................................... H05G 1/02
[52] U.S. Cl. .......................... 378/197; 378/98.8; 378/193
[58] Field of Search ..................... 378/167, 182, 378/177, 187, 193, 195, 196, 197, 198

[56] References Cited

U.S. PATENT DOCUMENTS 5,023,899 6/1991 Ohlson ................................ 378/197 X
5,166,968 11/1992 Morse .
5,185,777 2/1993 Hasegawa .

*Primary Examiner*—David P. Porta
*Attorney, Agent, or Firm*—Sughrue, Mion, Zinn, Macpeak & Seas, PLLC

[57] ABSTRACT

A medical X-ray system having a radiation source (5) and a radiation receiver (6) which receives radiation emitted by the source. The two components are arranged on a common support (7), the radiation receiver being mounted on the support in such a way that it can be detached and mounted to at least one further system component (11), in particular a wall bucky.

12 Claims, 3 Drawing Sheets

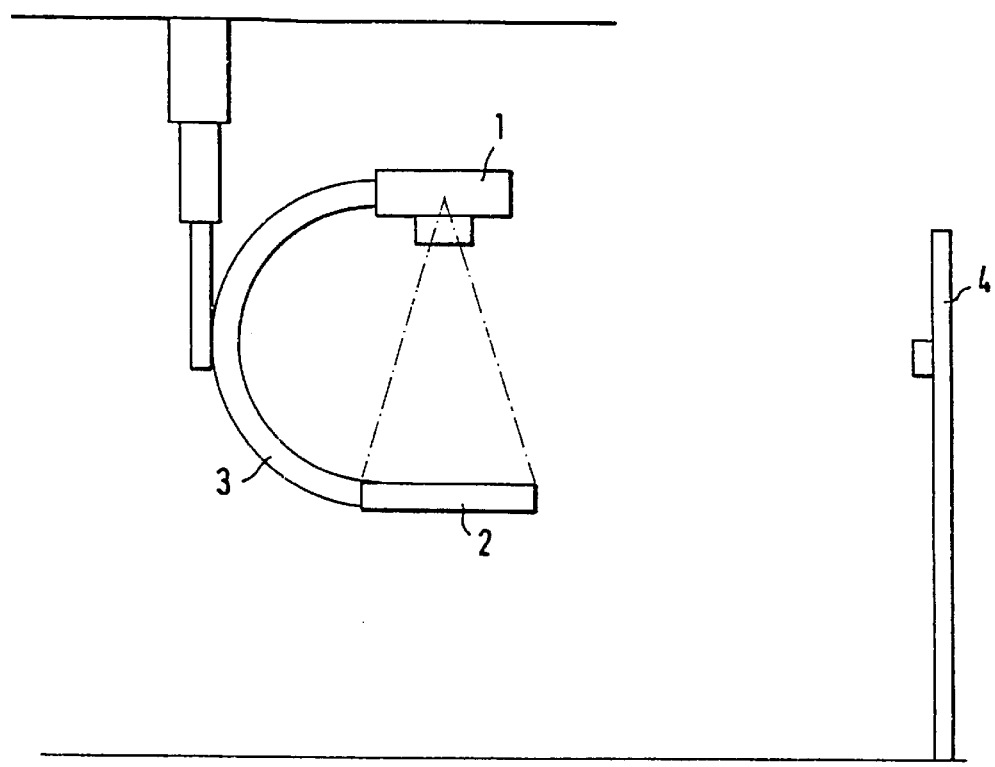
FIG. 4 CONVENTIONAL
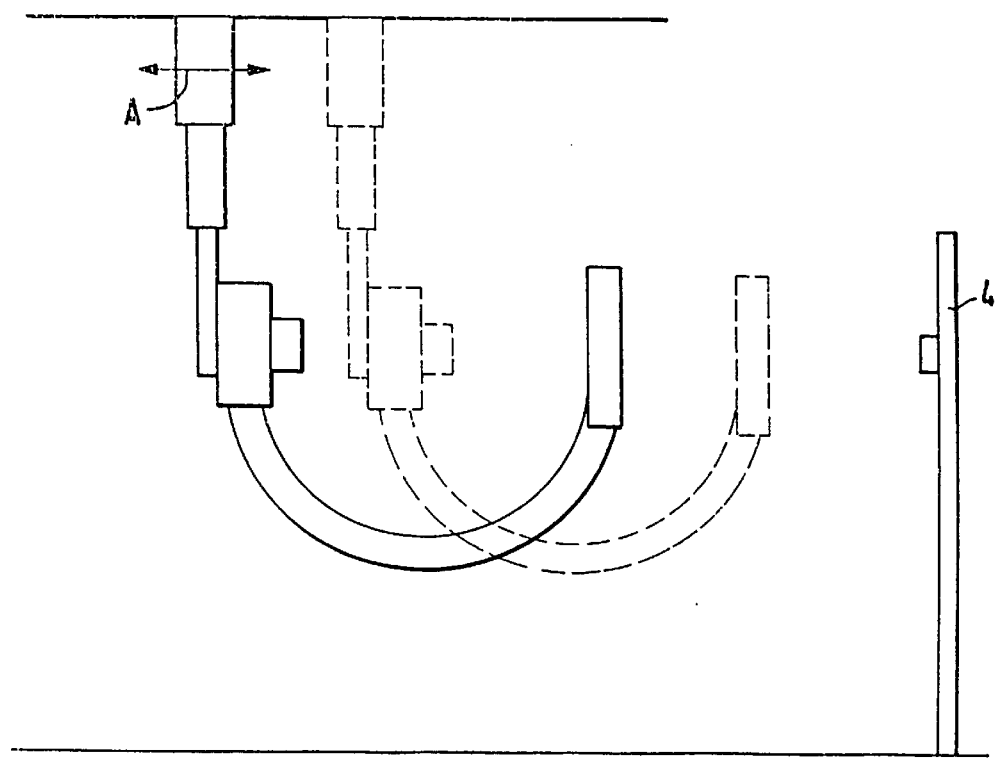
FIG. 5 CONVENTIONAL

MEDICAL X-RAY SYSTEM HAVING A COMMON SUPPORT AND A FURTHER COMPONENT FOR MOUNTING A RADIATION RECEIVER

The following disclosure is based on German Patent Application No. 19639977.7, filed on Sep. 27, 1997, which is incorporated into this application by reference.

FIELD OF AND BACKGROUND OF THE INVENTION

The invention relates to new and useful improvements in medical X-ray systems having a radiation source and a radiation receiver. More particularly, the invention relates to such a medical X-ray system in which the radiation source and receiver are arranged on a common support.

In such known X-ray systems, the radiation source, i.e. the X-ray tube, and the radiation receiver (for example a cassette grid drawer or a digital image receiver) are arranged on a common C-shaped or U-shaped support. The distance between them is therefore fixed. The range of examinations which can be carried out with the system is therefore limited to those for which this distance is adequate. Some examinations require a larger film-to-focus distance (for example about 180 cm in the case of chest X-rays). If the system is also to be used for these examinations, the system is normally provided with a second radiation receiver. The second receiver may be mounted on the wall, for example on a wall bucky. Providing the X-ray machine with two radiation receivers, one on the support and one on the wall bucky, naturally makes the machine more expensive. The additional costs are particularly high if the machine uses a digital radiation receiver in the form of an image detector, which is substantially more expensive than a cassette grid drawer.

OBJECTS OF THE INVENTION

It is therefore an object of the invention to provide an X-ray system with which it is possible to carry out a wider range of examinations than is possible with conventional, single receiver systems. It is a further object of the invention to provide a system that avoids the additional costs associated with incorporating more than one radiation receiver into the system.

SUMMARY OF THE INVENTION

These and other objects are achieved by the subject matter defined by claim 1. Particularly advantageous refinements of the invention are the subject matter of the dependent claims.

In a medical X-ray system of the above-described type, the problems associated with the conventional arrangement are solved according to the invention by designing the X-ray system to mount the radiation receiver on the support in a such a way it can be detached and mounted on at least one further system component. In particular, this further system component can be a wall bucky.

According to the invention, the radiation receiver (for example an expensive digital image sensor) can be mounted on the support in a first position so as to be rigidly coupled relative to the radiation source. Once coupled in this manner, the receiver can be moved in fixed relationship with the source by means of the support structure (for example a C-bar or a U-bracket). If, however, the system is to be used to take a chest X-ray, for example, the radiation receiver can be detached from the support and fitted to a further system component. This further component is preferably mounted on a wall of the examining room, for example as a wall bucky or the like. This enables a single system or a single examination room facility with a single detachable radiation receiver to perform a multiplicity of examinations, for which normally two radiation receivers would be required.

Moving the radiation receiver should be a straightforward procedure, particularly in hospitals, where speed is frequently critical in examining accident patients or the like. To meet this requirement, a further configuration of the invention uses a radiation receiver which is mounted with a snap-fit mechanism. The radiation receiver simply plugs into the support or the system component and latches there. Complex and time-consuming manual operations are consequently unnecessary.

According to one embodiment of the invention, the radiation receiver used is a digital image sensor. In this case it is expedient to design the snap-fit mechanism so that it provides both mechanical and electrical connection of the radiation receiver to the support or system component. This comprehensive mechanical and electrical connection carries, inter alia, both the power supply and the signals supplied by the image sensor. The support and system component, in turn, are provided with appropriate lines extending to the various electric and electronic components, e.g., a power supply, a console, a data memory and the like.

Certain methods of examination require pictures taken using oblique irradiation. Accordingly, a further configuration of the invention provides for such irradiations by mounting the radiation receiver on the support or system component so that it can pivot. The snap-fit mechanism can itself be pivotable.

The support is generally designed as a C-bar or U-bracket. When the radiation receiver is arranged elsewhere, it is important that the free end of the support, which would otherwise carry the radiation receiver, does not project into the X-ray beam emitted by the radiation source and thereby impair the picture. The invention prevents this by allowing the radiation source to be movable on the support, in particular longitudinally. The X-ray beam can then be kept clear of the projecting free end of the support by pivoting the radiation source or by moving it along the support.

In known X-ray systems, the support can generally be moved both horizontally and vertically. In order to achieve this same effect when the radiation detector is detached from the support and mounted instead on the system component, the invention mounts the radiation receiver on the system component so that it can move, in particular, vertically. The radiation receiver can thus be aligned with the radiation source when it is detached from the support. The ability to move the radiation receiver vertically on the system component is especially advantageous in situations where the radiation source is positioned low to the ground, e.g., in the case of a chest X-ray or the like of a child. The radiation source and the radiation receiver can be coupled and moved together by means of a servo-control when the receiver is mounted on the system component. Receiver and source preferably track each other automatically, e.g., through sensors and appropriate electronic control.

BRIEF DESCRIPTION OF THE DRAWINGS

The invention and further advantageous refinements of the invention according to the features of the dependent claims are explained in more detail below with the aid of diagrammatic, exemplary embodiments in the drawing, in which:

FIG. 4 shows a basic sketch of an X-ray system according to the conventional art, and FIG. 5 shows the system of FIG. 4 in a different typical position.

DETAILED DESCRIPTION OF THE PREFERRED EMBODIMENTS

The conventional art, shown in FIGS. 4 and 5, will be explained first. The advantages of the ring system according to the invention will then be discussed.

FIG. 4 shows an X-ray system comprising a radiation source 1 and an associated radiation receiver 2. These two components are rigidly coupled to one another on a common support 3, designed as a C-bar. The distance between the radiation source 1 and the radiation receiver 2 cannot be varied because of the rigid support coupling. This means that the film-to-focus distance is fixed. This can also be seen in FIG. 5, which shows the X-ray system of FIG. 4 in a position for taking horizontal pictures. The second position, shown by dashed lines, illustrates the horizontal movement of the system (in directions of double arrow A).

In order to use this system to take pictures with different film-to-focus distances, it is necessary to mount an additional radiation receiver on a system component, here in the form of a Bucky wall stand 4. The radiation source 1 is then aligned so that the X-ray radiation strikes this additional radiation receiver. The system thus requires two radiation receivers.

Figure 1:
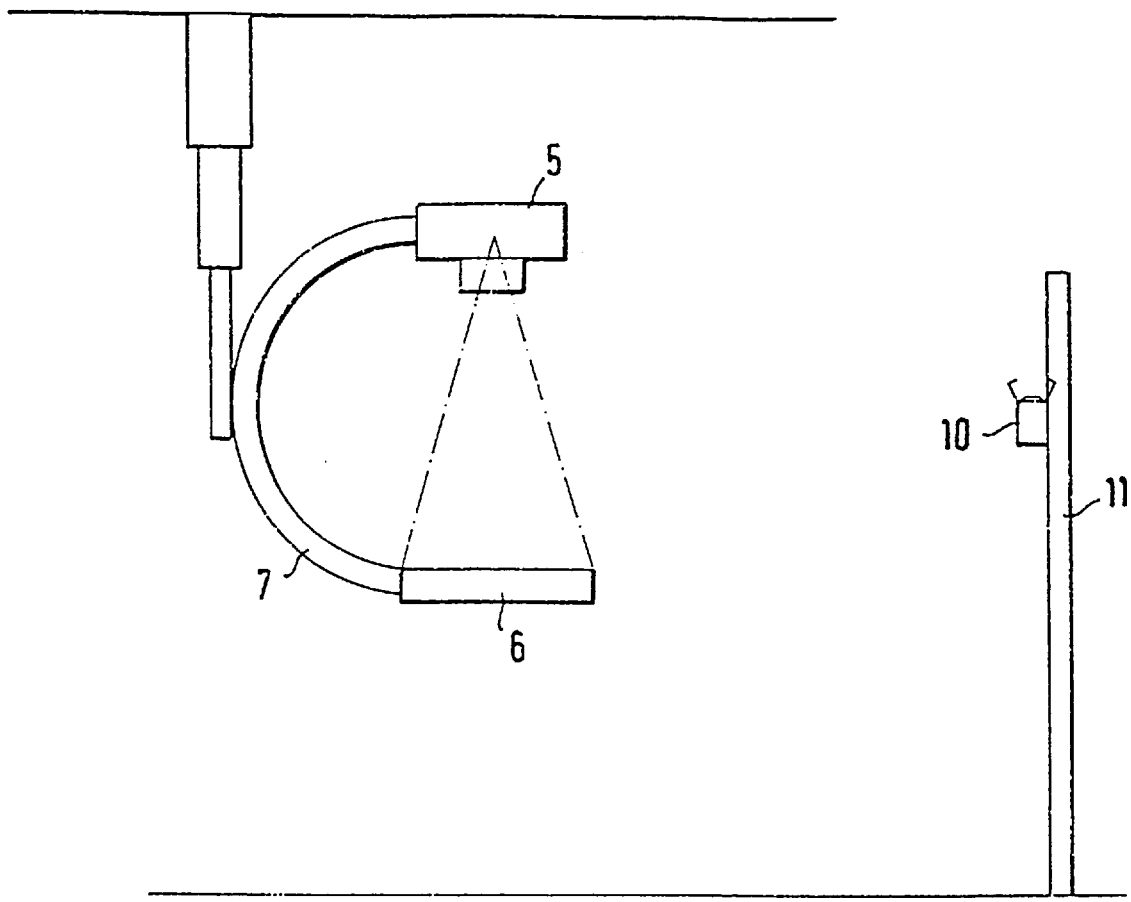
FIG. 1 shows a basic sketch of an x-ray system according to the invention.

The X-ray system of FIG. 1, which constitutes a first embodiment of the invention, also comprises a radiation source 5 and a radiation receiver 6 mounted on a common support 7. The radiation receiver 6 is, for example, a digital image sensor. According to the invention, a snap-fit mechanism, shown in simplified form in FIG. 2, makes it possible to detach the radiation receiver 6 from the support 7. This snap-fit mechanism 8 comprises a plug 9. As shown here, by way of example, the plug 9 is mounted on the radiation receiver 6, although it can be mounted on the support 7. The plug 9 is received by a socket 10 which, according to the embodiment shown, is provided on the support 7 and on a remote system component. The remote system component is a Bucky wall 11 in the exemplary embodiment shown in FIG. 1. The plug 9 simply plugs into this socket 10 and latches there.

If the radiation receiver 6 is fashioned as a digital image sensor, the interconnection between the socket 10 and the plug 9 also preferably establishes an electrical and/or electronic connection to the digital image sensor. The snap-fit connection supplies current to the sensor and also loops through both the signals supplied by the sensor and the control signals destined for it. A socket 10 of this same type is also mounted on the Bucky wall 11, as shown in FIG. 1.

Figure 2:
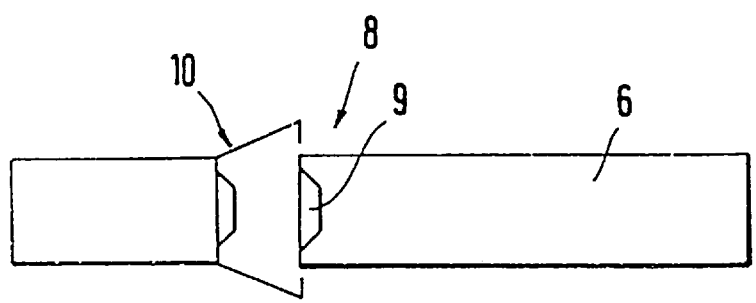
FIG. 2 shows a basic sketch of a snap-fit mechanism for mounting a detachable radiation receiver.

The embodiment of FIG. 2 provides only a single snap-fit connection. It is, however, also possible to fasten the radiation receiver with a connection utilizing multiple plugs. This improves stability, since a digital image sensor conventionally weighs up to about 20 kg.

Figure 3:
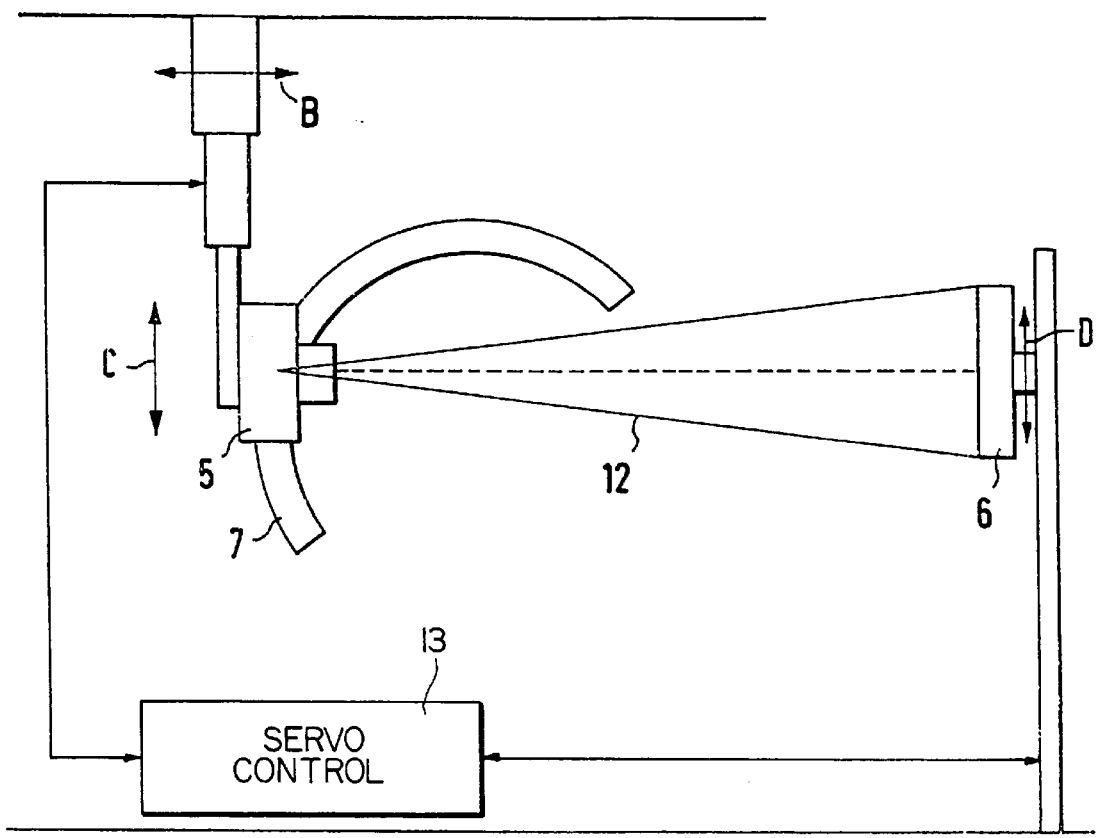
FIG. 3 shows a basic sketch of the X-ray system with the radiation receiver mounted on a system component.

The basic arrangement shown in FIG. 1 is further able to take chest X-rays, which require a larger film-to-focus distance (about 180cm) than the support 7 can accommodate. This is achieved by removing the radiation receiver 6 from the support 7 by means of the snap-fit mechanism and plugging it into the socket 10 on the Bucky wall 11. As schematically shown in FIG. 3, the radiation source 5 is then appropriately positioned by moving it horizontally (in the directions of double arrow B) and vertically (in the directions of double arrow C) and shifting it along the support 7. The radiation source 5 is positioned so that it is opposite, and centralized with respect to, the radiation receiver 6. The two components are, of course, also aligned with respect to the object to be examined. As FIG. 3 shows, the support 7 is positioned so that it does not project into the beam path 12 of the radiation source 5.

As FIG. 3 also shows, the radiation receiver 6 can be moved vertically (in the directions of double arrow D) to set the appropriate height for the receiver 6. According to a preferred embodiment a servo control 13 is provided for automating the procedure for aligning the radiation source and receiver. This can be performed, for instance, through appropriate sensors and drives operating according to a master/slave protocol, whereby, e.g., the radiation receiver 6 mimics movements of the radiation source 5. At the end of the examination, the radiation receiver 6 is then detached again from the socket 10 on the wall bucky 11 and returned to the socket 10 on the support 7.

The above description of the preferred embodiments has been given by way of example. From the disclosure given, those skilled in the art will not only understand the present invention and its attendant advantages, but will also find apparent various changes and modifications to the structures disclosed. It is sought, therefore, to cover all such changes and modifications as fall within the spirit and scope of the invention, as defined by the appended claims, and equivalents thereof.

What is claimed is:

1. A medical X-ray system comprising:

a radiation source;

a digital image sensor, for receiving radiation emitted by said radiation source;

a common support arranged to support said radiation source and said digital image sensor; and a further system component;

wherein said common support is configured to mount said digital image sensor directly and detachably on said common support;

wherein said further system component is configured to mount said digital image sensor directly and detachably on said further system component;

wherein said common support comprises a first pivot mount for pivotably and detachably fastening said digital image sensor to said commmon support; and wherein said further system component comprises a further pivot mount for pivotably and detachably fastening said digital image sensor to said further system component.

2. The medical X-ray system as claimed in claim 1, wherein said further system component comprises a wall bucky.

3. The medical X-ray system as claimed in claim 1, wherein said common support is further configured to mount said radiation source at plural positions longitudinally along said common support.

4. The medical X-ray system as claimed in claim 1, wherein said further system component is further configured to mount said digital image source at plural positions vertically along said further system component.

5. The medical X-ray system as claimed in claim 4, wherein said common support is further configured to mount said radiation source at plural positions corresponding substantially to the plural positions along said further system component; and further comprising a servo-control for maintaining a substantially fixed relative positioning between said radiation source and said digital image source.

6. A medical X-ray system comprising:

a radiation source;

a radiation receiver for receiving radiation emitted by said radiation source;

a common support arranged to support said radiation source and said radiation receiver; and a further system component;

wherein said common support is configured to mount said radiation receiver detachably on said common support;

wherein said further system component is configured to mount said radiation receiver detachably on said further system component;

wherein said common support comprises a first snap-fit mechanism for detachably fastening said radiation receiver to said common support; and wherein said further system component comprises a further snap fit mechanism for detachably fastening said radiation receiver to said further system component.

7. The medical X-ray system as claimed in claim 6, wherein said radiation receiver comprises a digital image sensor; and wherein said first snap-fit mechanism is configured to produce a mechanical and an electrical connection of said digital image sensor to said common support when said digital image sensor is mounted on said common support; and wherein said further snap-fit mechanism is configured to produce a mechanical and an electrical connection of said digital image sensor to said further system component when said digital image sensor is mounted on said further system component.

8. The medical X-ray system as claimed in claim 6, wherein said first snap-fit mechanism comprises a first pivot mount for pivotably and detachably fastening said radiation receiver to said common support; and wherein said further snap-fit mechanism comprises a further pivot mount for pivotably and detachably fastening said radiation receiver to said further system component.

9. The medical X-ray system as claimed in claim 6, wherein said further system component comprises a wall bucky.

10. The medical X-ray system as claimed in claim 6, wherein said common support is further configured to mount said radiation source at plural positions longitudinally along said common support.

11. The medical X-ray system as claimed in claim 6, wherein said further system component is further configured to mount said radiation receiver at plural positions vertically along said further system component.

12. The medical X-ray system as claimed in claim 11, wherein said common support is further configured to mount said radiation source at plural positions corresponding substantially to the plural positions along said further system component; and further comprising a servo-control for maintaining a substantially fixed relative positioning between said radiation source and said radiation receiver.

* * * * *